United States Patent
Stach et al.

[11] 4,073,894
[45] Feb. 14, 1978

[54] OXADIAZOLIDINE SUBSTITUTED PHOSPHORUS COMPOUNDS

[75] Inventors: Leonard J. Stach, Riverside; Robert N. Wilke, Chicago, both of Ill.

[73] Assignee: Velsicol Chemical Corporation, Chicago, Ill.

[21] Appl. No.: 742,970

[22] Filed: Nov. 17, 1976

Related U.S. Application Data

[63] Continuation-in-part of Ser. No. 656,493, Feb. 23, 1976, abandoned.

[51] Int. Cl.$^2$ .................... C07D 271/06; A01N 9/36
[52] U.S. Cl. ................................ 424/200; 260/307 B
[58] Field of Search .................... 260/307 B; 424/200

[56] References Cited

U.S. PATENT DOCUMENTS 3,534,057  10/1970  Krenzer ........................... 260/306.7

*Primary Examiner*—Raymond V. Rush
*Attorney, Agent, or Firm*—Robert J. Schwarz; Dietmar Olesch

[57] ABSTRACT

This invention discloses new compounds of the formula

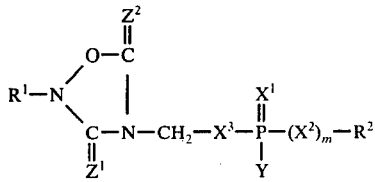

wherein $R^1$ and $R^2$ are independently selected from the group consisting of alkyl and

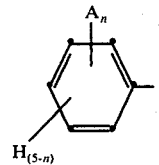

wherein A is selected from the group consisting of alkyl, alkoxy, alkylthio, halogen, nitro and cyano; and $n$ is an integer from 0 to 3; $X^1$, $X^2$, $X^3$, $Z^1$ and $Z^2$ are independently selected from the group consisting of oxygen and sulfur; $m$ is the integer 0 or 1; and Y is selected from the group consisting of alkyl, alkoxy, alkylthio, amino, alkylamino and dialkylamino. Further disclosed are insecticidal compositions containing as an essential ingredient a compound of the foregoing description.

10 Claims, No Drawings

OXADIAZOLIDINE SUBSTITUTED PHOSPHORUS COMPOUNDS

This application is a continuation-in-part of our copending application, Ser. No. 656,493, filed Feb. 23, 1976, now abandoned.

This invention relates to new compositions of matter and more specifically relates to new chemical compounds of the formula

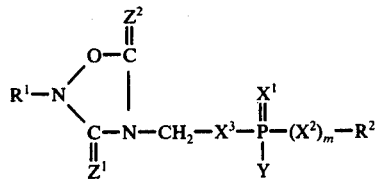
(I)

wherein $R^1$ and $R^2$ are independently selected from the group consisting of alkyl and

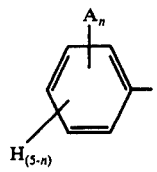

wherein A is selected from the group consisting of alkyl, alkoxy, alkylthio, halogen, nitro and cyano; and $n$ is an integer from 0 to 3; $X^1$, $X^2$, $X^3$, $Z^1$ and $Z^2$ are independently selected from the group consisting of oxygen and sulfur; $m$ is the integer 0 or 1; and Y is selected from the group consisting of alkyl, alkoxy, alkylthio, amino, alkylamino and dialkylamino.

The compounds of the present invention are unexpectedly useful as insecticides.

In a preferred embodiment of this invention $R^1$ and $R^2$ are independently selected from the group consisting of lower alkyl and

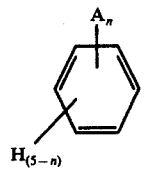

wherein A is selected from the group consisting of lower alkyl, lower alkoxy, lower alkylthio and halogen; and $n$ is an integer from 0 to 2; $X^1$, $X^2$, $X^3$, $Z^1$ and $Z^2$ are independently selected from the group consisting of oxygen and sulfur; $m$ is the integer 0 or 1; and Y is selected from the group consisting of lower alkyl, lower alkoxy, lower alkylthio, amino, lower alkylamino and di(lower alkyl)amino.

The compounds of the present invention can be readily prepared by reacting an oxadiazolidine of the formula

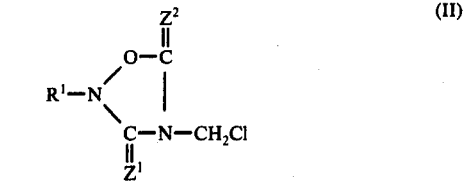
(II)

wherein $R^1$, $Z^1$ and $Z^2$ are as heretofore described, with an about equimolar amount of a phosphorus compound of the formula

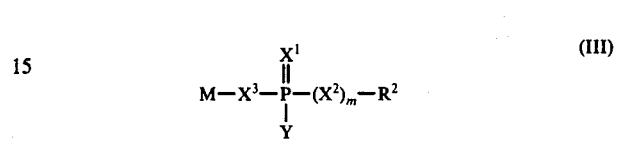
(III)

wherein M is an alkali metal such as potassium or sodium and $X^1$, $X^2$, $X^3$, Y, $R^2$ and $m$ are as heretofore described. This reaction can be effected by combining the compounds of formulae II and III in an inert organic reaction medium such as acetonitrile at room temperature and stirring the resulting mixture for a period of from 4 to 24 hours. After this time the reaction mixture is filtered to remove alkali metal chloride and the filtrate is stripped of solvent to yield the desired product as a residue. This product can then be used as such or can be further purified by washing, extraction or other standard techniques in the art.

The compounds of formula II can be prepared by reaction a compound of the formula

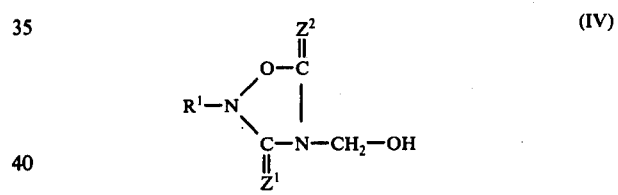
(IV)

wherein $R^1$, $Z^1$ and $Z^2$ are as heretofore described, with an excess molar amount of thionyl chloride. This reaction can be carried out by combining a solution of a molar amount of the compound of formula IV in an inert organic solvent such as chloroform with about two molar amounts of thionyl chloride also dissolved in an inert organic solvent such as chloroform. The reaction mixture can then be heated at reflux with stirring for a period of from ½ to about 8 hours. After this time the reaction mixture is stripped of solvent to yield the desired product as a solid residue. This product can then be used as such or can be further purified by washing, recrystallizing and the like.

The compounds of formula IV can be prepared by reacting a compound of the formula

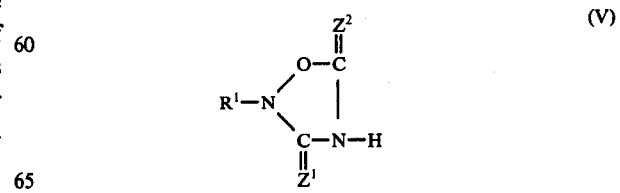
(V)

wherein $R^1$, $Z^1$ and $Z^2$ are as heretofore described, with formaldehyde. This reaction can be carried out by combining a solution of the compound of formula V in an inert, water-miscible, organic solvent such as methanol with an excess molar amount of aqueous formaldehyde. The reaction mixture can then be heated at reflux for a period of about ½ to about 6 hours. After this time the reaction mixture can be stripped of solvents and the residue dissolved in methylene chloride. The resulting solution can then be washed with water, dried and stripped of solvent to yield the desired product.

The compounds of formula V as well as those of formula III are known in the art.

The manner in which the compounds of the present invention can be prepared is more specifically illustrated in the following examples.

EXAMPLE 1

Preparation of 2-Phenyl-4-hydroxymethyl-1,2,4-oxadiazolidin-3,5-dione

2-Phenyl-1,2,4-oxadiazolidin-3,5-dione (6.75 grams; 0.044 mole) dissolved in methanol (100 ml) and aqueous formaldehyde (5.67 ml of 37% conc.; 0.06 mole) were charged into a glass reaction vessel equipped with a mechanical stirrer, thermometer and reflux condenser. The reaction mixture was heated at reflux, with stirring for a period of about 2 hours. After this time the reaction mixture was stripped of methanol and water to yield a solid residue. The residue was then dissolved in methylene chloride, and the resulting solution was washed with water. The washed solution was dried over anhydrous magnesium sulfate and stripped of solvent to yield the desired product 2-phenyl-4-hydroxymethyl-1,2,4-oxadiazolidin-3,5-dione as a solid residue.

EXAMPLE 2

Preparation of 2-Phenyl-4-chloromethyl-1,2,4-oxadiazolidin-3,5-dione

2-Phenyl-4-hydroxymethyl-1,2,4-oxadiazolidin-3,5-dione (7.6 grams; 0.0365 mole) dissolved in chloroform (40 ml) and thionyl chloride (8.68 grams; 0.073 mole) dissolved in chloroform (10 ml) were charged into a glass reaction vessel equipped with a mechanical stirrer, thermometer and reflux condenser. The reaction mixture was heated at reflux with stirring for a period of about 2 hours. After this time the reaction mixture was stripped of solvent under reduced pressure, leaving a solid residue. This residue was dissolved in toluene and was distilled to remove unreacted starting material. The remaining product was recrystallized from a hexane-ether mixture to yield the desired product 2-phenyl-4-chloromethyl-1,2,4-oxadiazolidin-3,5-dione.

EXAMPLE 3

Preparation of S-(2-Phenyl-1,2,4-oxadiazolidin-3,5-dion-4-ylmethyl) O-Methyl N-Isopropylthiolophosphoramidate 2-Phenyl-4-chloromethyl-1,2,4-oxadiazolidin-3,5-dione (2.0 grams; 0.0088 mole) dissolved in acetonitrile (25 ml) was charged into a glass reaction vessel equipped with a mechanical stirrer. S-Potassium O-methyl N-isopropylthiolophosphoramidate (1.86 grams; 0.0097 mole) was added to the reaction vessel, and the mixture was stirred at room temperature overnight. After this time the reaction mixture was filtered to remove potassium chloride precipitate. The precipitate was washed with methylene chloride, and the washings were combined with the filtrate. The combined solutions were then stripped of solvents, leaving an oil. This oil was dissolved in chloroform, and the resulting solution was filtered. The filtrate was stripped of solvent to yield the desired product S-(2-phenyl-1,2,4-oxadiazolidin-3,5-dion-4-ylmethyl) O-methyl N-isopropylthiolophosphoramidate as a viscous oil.

EXAMPLE 4

Preparation of S-(2-Phenyl-1,2,4-oxadiazolidin-3,5-dion-4-ylmethyl) O,O-Diethyl Thiolothionophosphate 2-Phenyl-4-chloromethyl-1,2,4-oxadiazolidin-3,5-dione (2.8 grams; 0.0124 mole) dissolved in acetonitrile (25 ml) was charged into a glass reaction vessel equipped with a mechanical stirrer. S-Potassium O,O-diethyl thiolothionophosphoramidate (3.06 grams; 0.013 mole) was added to the reaction vessel, and the mixture was stirred at room temperature overnight. After this time the reaction mixture was filtered to remove potassium chloride precipitate. The precipitate was washed with methylene chloride, and the washings were combined with the filtrate. The combined solutions were then stripped of solvents, leaving an oil. This oil was dissolved in methylene chloride, and the resulting solution was washed with water and dried over anhydrous magnesium sulfate. The dried solution was stripped of solvent, leaving a viscous oil. This oil was dissolved in ethyl ether and was filtered. The filtrate was then stripped of solvent under reduced pressure to yield a yellow oil. The oil was then dissolved in ether, was washed with water and aqueous sodium carbonate, was dried and stripped of ether under vacuum to yield an oil. This oil solidified upon standing to yield the desired product S-(2-phenyl-1,2,4-oxadiazolidin-3,5-dion-4-ylmethyl) O,O-diethyl thiolothionophosphate as a low melting solid.

EXAMPLE 5

Preparation of 2-Methyl-5-hydroxymethyl-1,2,4-oxadiazolidin-3,5-dione

2-Methyl-1,2,4-oxadiazolidin-3,5-dione (2.0 grams; 0.0172 mole) dissolved in methanol (100 ml) and aqueous formaldehyde (2.5 ml of 37% conc.; 0.0344 mole) were charged into a glass reaction vessel equipped with a mechanical stirrer. The reaction mixture was stirred overnight. After this time the reaction mixture was stripped of methanol and water to yield an oil. The oil was then dissolved in methylene chloride, and the resulting solution was washed with water. The washed solution was dried over anhydrous magnesium sulfate and stripped of solvent to yield the desired product 2-methyl-4-hydroxymethyl-1,2,4-oxadiazolidin-3,5-dione as an oil.

EXAMPLE 6

Preparation of
2-Methyl-4-chloromethyl-1,2,4-oxadiazolidin-3,5-dione

2-Methyl-4-hydroxymethyl-1,2,4-oxadiazolidin-3,5-dione (2.5 grams) dissolved in chloroform (20 ml) and thionyl chloride (4.09 grams; 0.034 mole) dissolved in chloroform (5 ml) were charged into a glass reaction vessel equipped with a mechanical stirrer, thermometer and reflux condenser. The reaction mixture was heated at reflux with stirring for a period of about 2 hours.

After this time the reaction mixture was stripped of solvent under reduced pressure, leaving an oil. This oil was dissolved in toluene and was distilled to yield the desired product 2-methyl-4-chloromethyl-1,2,4-oxadiazolidin-3,5-dione as a reddish oil.

EXAMPLE 7

Preparation of
S-(2-Methyl-1,2,4-oxadiazolidin-3,5-dion-4-ylmethyl) O-Methyl N-Isopropylthiolophosphoramidate 2-Methyl-4-chloromethyl-1,2,4-oxadiazolidin-3,5-dione (2.7 grams; 0.0164 mole) dissolved in acetonitrile (30 ml) was charged into a glass reaction vessel equipped with a mechanical stirrer. S-Potassium O-methyl N-isopropylthiolophosphoramidate (4.05 grams; 0.0195 mole) was added to the reaction vessel, and the mixture was stirred at room temperature overnight. After this time the reaction mixture was filtered to remove potassium chloride precipitate. The precipitate was washed with methylene chloride, and the washings were combined with the filtrate. The combined solutions were then stripped of solvents, leaving an oil. This oil was dissolved in chloroform, and the resulting solution was filtered. The filtrate was stripped of solvent, leaving a viscous oil. This oil was dissolved in ether and was filtered. The filtrate was stripped of solvent to yield the desired product S-(2-methyl-1,2,4-oxadiazolidin-3,5-dion-4-ylmethyl) O-methyl N-isopropylthiolophosphoramidate.

EXAMPLE 8

Preparation of
S-(2-Methyl-1,2,4-oxadiazolidin-3,5-dion-4-ylmethyl) O,O-Diethyl Thiolothionophosphate 2-Methyl-4-chloromethyl-1,2,4-oxadiazolidin-3,5-dione (2.0 grams; 0.0121 mole) dissolved in acetonitrile (20 ml) was charged into a glass reaction vessel equipped with a mechanical stirrer. S-Potassium O,O-diethyl thiolothionophosphoramidate (2.99 grams; 0.0133 mole) was added to the reaction vessel, and the mixture was stirred at room temperature overnight. After this time the reaction mixture was filtered to remove potassium chloride precipitate. The precipitate was washed with methylene chloride, and the washings were combined with the filtrate. The combined solutions were then stripped of solvents, leaving an oil. This oil was dissolved in ether, and the resulting solution was filtered. The filtrate was stripped of solvent to yield a viscous oil. This oil was dissolved in chloroform, filtered, and the filtrate washed with water, dried and stripped of solvent to yield the desired product S-(2-methyl-1,2,4-oxadiazolidin-3,5-dion-4-ylmethyl) O,O-diethyl thiolothionophosphate as an oil.

EXAMPLE 9

Preparation of
2-(4-Methylphenyl)-4-hydroxymethyl-1,2,4-oxadiazolidin-3,5-dione 2-(4-Methylphenyl)-1,2,4-oxadiazolidin-3,5-dione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(4-methylphenyl)-4-hydroxymethyl-1,2,4-oxadiazolidin-3,5-dione.

EXAMPLE 10

Preparation of
2-(4-Methylphenyl)-4-chloromethyl-1,2,4-oxadiazolidin-3,5-dione 2-(4-Methylphenyl)-4-hydroxymethyl-1,2,4-oxadiazolidin-3,5-dione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. After this time the reaction mixture is stripped of solvent under reduced pressure, leaving a residue. This residue is dissolved in toluene, and the toluene solution is stripped of solvent and unreacted starting materials to yield the desired product 2-(4-methylphenyl)-4-chloromethyl-1,2,4-oxadiazolidin-3,5-dione as the residue.

EXAMPLE 11

Preparation of
S-[2-(4-Methylphenyl)-1,2,4-oxadiazolidin-3,5-dion-4-ylmethyl] O-(3,4-Dichlorophenyl) N,N-Dimethylthiolophosphoramidate 2-(4-Methylphenyl)-4-chloromethyl-1,2,4-oxadiazolidin-3,5-dione (0.02 mole) is dissolved in acetonitrile (35 ml) and is charged into a glass reaction vessel equipped with a mechanical stirrer. S-Potassium O-(3,4-dichlorophenyl) N,N-dimethylthiolophosphoramidate (0.023 mole) is added to the reaction vessel, and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered, and the filtrate is stripped of solvent to yield the desired product S-[2-(4-methylphenyl)-1,2,4-oxadiazolidin-3,5-dion-4-ylmethyl] O-3,4-dichlorophenyl) N,N-dimethylthiolophosphoramidate as the residue.

EXAMPLE 12

Preparation of
2-(4-Methoxyphenyl)-4-hydroxymethyl-1,2,4-oxadiazolidin-3,5-dione 2-(4-Methoxyphenyl)-1,2,4-oxadiazolidin-3,5-dione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(4-methoxyphenyl)-4-hydroxymethyl-1,2,4-oxadiazolidin-3,5-dione.

EXAMPLE 13

Preparation of
2-(4-Methoxyphenyl)-4-chloromethyl-1,2,4-oxadiazolidin-3,5-dione 2-(4-Methoxyphenyl)-4-hydroxymethyl-1,2,4-oxadiazolidin-3,5-dione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. After this time the reaction mixture is stripped of solvent under reduced pressure, leaving a residue. This residue is dissolved in toluene, and the toluene solution is stripped of solvent and unreacted starting materials to yield the desired product 2-(4-methoxyphenyl)-4-chloromethyl-1,2,4-oxadiazolidin-3,5-dione as the residue.

EXAMPLE 14

Preparation of
S-[2-(4-Methoxyphenyl)1,2,4-oxadiazolidin-3,5-dion-4-ylmethyl] S-(4-Methylphenyl) O-Methyl Dithiolophosphate 2-(4-Methoxyphenyl)-4-chloromethyl-1,2,4-oxadiazolidin-3,5-dione (0.02 mole) is dissolved in acetonitrile (35 ml) and is charged into a glass reaction vessel equipped with a mechanical stirrer. S-Potassium S-(4-methylphenyl) O-methyl dithiolophosphate (0.023 mole) is added to the reaction vessel, and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered, and the filtrate is stripped of solvent to yield the desired product S-[2-(4-methoxyphenyl)-1,2,4-oxadiazolidin-3,5-dion-4-ylmethyl] S-(4-methylphenyl) O-methyl dithiolophosphate as the residue.

EXAMPLE 15

Preparation of
2-(3-Methylthiophenyl)-4-hydroxymethyl-1,2,4-oxadiazolidin-3,5-dione 2-(3-methylthiophenyl)-1,2,4-oxadiazolidin-3,5-dione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(3-methylthiophenyl)-4-hydroxymethyl-1,2,4-oxadiazolidin-3,5-dione.

EXAMPLE 16

Preparation of
2-(3-Methylthiophenyl)-4-chloromethyl-1,2,4-oxadiazolidin-3,5-dione 2-(3-Methylthiophenyl)-4-hydroxymethyl-1,2,4-oxadiazolidin-3,5-dione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. After this time the reaction mixture is stripped of solvent under reduced pressure, leaving a residue. This residue is dissolved in toluene, and the toluene solution is stripped of solvent and unreacted starting materials to yield the desired product 2-(3-methylthiophenyl)-4-chloromethyl-1,2,4-oxadiazolidin-3,5-dione as the residue.

EXAMPLE 17

Preparation of
S-[2-(3-Methylthiophenyl)-1,2,4-oxadiazolidin-3,5-dion-4-ylmethyl] S-Ethyl O-(4-Methoxyphenyl) Dithiolophosphate 2-(3-Methylthiophenyl)-4-chloromethyl-1,2,4-oxadiazolidin-3,5-dione (0.02 mole) is dissolved in acetonitrile (35 ml) and is charged into a glass reaction vessel equipped with a mechanical stirrer. S-Potassium S-ethyl O-(4-methoxyphenyl) dithiolophosphate (0.023 mole) is added to the reaction vessel, and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered, and the filtrate is stripped of solvent to yield the desired product S-[2-(3-methylthiophenyl)-1,2,4-oxadiazolidin-3,5-dion-4-ylmethyl] S-ethyl O-(4-methoxyphenyl) dithiolophosphate as the residue.

EXAMPLE 18

Preparation of
2-(3,4-Dichlorophenyl)-4-hydroxymethyl-1,2,4-oxadiazolidin-3,5-dione 2-(3,4-Dichlorophenyl)-1,2,4-oxadiazolidin-3,5-dione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(3,4-dichlorophenyl)-4-hydroxymethyl-1,2,4-oxadiazolidin-3,5-dione.

EXAMPLE 19

Preparation of 2-(3,4-Dichlorophenyl)-4-chloromethyl-1,2,4-oxadiazolidin-3,5-dione 2-(3,4-Dichlorophenyl)-4-hydroxymethyl-1,2,4-oxadiazolidin-3,5-dione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. After this time the reaction mixture is stripped of solvent under reduced pressure, leaving a residue. This residue is dissolved in toluene, and the toluene solution is stripped of solvent and unreacted starting materials to yield the desired product 2-(3,4-dichloropheny)-4-chloromethyl-1,2,4-oxadiazolidin-3,5-dione as the residue.

EXAMPLE 20

Preparation of O-[2-(3,4-Dichlorophenyl)-1,2,4-oxadiazolidin-3,4-dion-4-ylmethyl] O-(4-Cyanophenyl) Methylphosphonate 2-(3,4-Dichlorophenyl)-4-chloromethyl-1,2,4-oxadiazolidin-3,5-dione (0.02 mole) is dissolved in acetonitrile (35 ml) and is charged into a glass reaction vessel equipped with a mechanical stirrer. O-Potassium O-(4-cyanophenyl) methylphosphonate (0.023 mole) is added to the reaction vessel, and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered, and the filtrate is stripped of solvent to yield the desired product O-[2-(3,4-dichlorophenyl)-1,2,4-oxadiazolidin-3,5-dion-4-ylmethyl] O-(4-cyanophenyl) methylphosphonate as the residue.

EXAMPLE 21

Preparation of 2-(2,6-Dinitrophenyl)-4-hydroxymethyl-1,2,4-oxadiazolidin-3,5-dione 2-(2,6-Dinitrophenyl)-1,2,4-oxadiazolidin-3,5-dione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(2,6-dinitrophenyl)-4-hydroxymethyl-1,2,4-oxadiazolidin-3,5-dione.

EXAMPLE 22

Preparation of 2-(2,6-Dinitrophenyl)-4-chloromethyl-1,2,4-oxadiazolidin-3,5-dione 2-(2,6-Dinitrophenyl)-4-hydroxymethyl-1,2,4-oxadiazolidin-3,5-dione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. Aftr this time the reaction mixture is stripped of solvent under reduced pressure, leaving a residue. This residue is dissolved in toluene, and the toluene solution is stripped of solvent and unreacted starting materials to yield the desired product 2-(2,6-dinitrophenyl)-4-chloromethyl-1,2,4-oxadiazolidin-3,5-dione as the residue.

EXAMPLE 23

Preparation of O-[2-(2,6-Dinitrophenyl)-1,2,4-oxadiazolidin-3,5-dion-4-ylmethyl] S-(3-Methylthiophenyl) N-t-Butylthiolothionophosphoramidate 2-(2,6-Dinitrophenyl)-4-chloromethyl-1,2,4-oxadiazolidin-3,5-dione (0.02 mole) is dissolved in acetonitrile (35 ml) and is charged into a glass reaction vessel equipped with a mechanical stirrer. O-Potassium S-(3-methylthiophenyl) N-t-butylthiolothionophosphoramidate (0.023 mole) is added to the reaction vessel, and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered and the filtrate is stripped of solvent to yield the desired product O-[2-(2,6-dinitrophenyl)-1,2,4-oxadiazolidin-3,5-dion-4-ylmethyl] S-(3-methylthiophenyl) N-t-butylthiolothionophosphoramidate as the residue.

EXAMPLE 24

Preparation of 2-(4-Cyanophenyl)-4-hydroxymethyl-1,2,4-oxadiazolidin-3,5-dithione 2-(4-Cyanophenyl)-1,2,4-oxadiazolidin-3,5-dithione (0.05 mole) dissolved in methanol (100 ml) and aqueous formaldehyde (37% conc.; 0.06 mole) are charged into a glass reaction vessel equipped with a mechanical stirrer, thermometer and reflux condenser. The reaction mixture is heated at reflux, with stirring for a period of about 2 hours. After this time the reaction mixture is stripped of methanol and water, leaving a residue. This residue is dissolved in methylene chloride, and the resulting solution is washed with water. The washed solution is dried over anhydrous magnesium sulfate, filtered and stripped of solvent to yield the desired product 2-(4-cyanophenyl)-4-hydroxymethyl-1,2,4-oxadiazolidin-3,5-dithione.

EXAMPLE 25

Preparation of 2-(4-Cyanophenyl)-4-chloromethyl-1,2,4-oxadiazolidin-3,5-dithione 2-(4-Cyanophenyl)-4-hydroxymethyl-1,2,4-oxadiazolidin-3,5-dithione (0.03 mole) dissolved in chloroform (40 ml) and thionyl chloride (0.06 mole) dissolved in chloroform (10 ml) are charged into a glass reaction vessel equipped with a mechanical stirrer, thermometer and reflux condenser. The reaction mixture is heated at reflux for a period of about 2 hours. After this time the reaction mixture is stripped of solvent under reduced pressure, leaving a residue. This residue is dissolved in toluene, and the toluene solution is stripped of solvent and unreacted starting materials to yield the desired product 2-(4-cyanophenyl)-4-chloromethyl-1,2,4-oxadiazolidin-3,5-dithione as the residue.

EXAMPLE 26

Preparation of S-[2-(4-Cyanophenyl)-1,2,4-oxadiazolidin-3,5-dithion-4-ylmethyl] O-(3-Nitrophenyl) O-Ethyl Thiolothionophosphate 2-(4-Cyanophenyl)-4-chloromethyl-1,2,4-oxadiazolidin-3,5-dithione (0.02 mole) is dissolved in acetonitrile (35 ml) and is charged into a glass reaction vessel equipped with a mechanical stirrer. S-Potassium O-(3-nitrophenyl) thiolothionophosphate (0.023 mole) is added to the reaction vessel and the mixture is stirred at room temperature for a period of about 12 hours. After this time the reaction mixture is filtered to remove potassium chloride precipitate. The precipitate is washed with methylene chloride, and the washings are combined with the filtrate. The combined solution is then stripped of solvents, and the residue is redissolved in chloroform. The chloroform solution is filtered, and the filtrate is stripped of solvent to yield the desired product S-[2-(4-cyanophenyl)-1,2,4-oxadiazolidin-3,5-dithion-4-ylmethyl] O-(3-nitrophenyl) O-ethyl thiolothionophosphate as the residue.

Additional compounds within the scope of the present invention which can be prepared by the procedures detailed in the foregoing examples are exemplified by the following: S-[2-(4-fluorophenyl)-1,2,4-oxadiazolidin-3,5-dithion-4-ylmethyl] O-(2-bromo-4-ethylphenyl) isopropylthiolophosphonate, S-[2-(3,4-dibromophenyl)-1,2,4-oxadiazolidin-3,5-dion-4-ylmethyl] O-(3-ethoxyphenyl) t-butylthiolophosphonate, S-[2-(4-iodophenyl)-1,2,4-oxadiazolidin-3,5-dion-4-ylmethyl] O-(2-butoxyphenyl) pentylthiolophosphonate, S-[2-(3-ethylthiophenyl)-1,2,4-oxadiazolidin-3,5-dion-4-ylmethyl] O-(4-hexyloxyphenyl) hexylthiolophosphonate, S-[2-(4-propylthiophenyl)-1,2,4-oxadiazolidin-3,5-dion-4-ylmethyl] O-(2-ethylthiophenyl) O-propyl thiolophosphate, S-[2-(4-hexylthiophenyl)-1,2,4-oxadiazolidin-3,5-dion-4-ylmethyl] O-(3-propylthiophenyl) O-butyl thiolophosphate, S-[2-(3-ethoxyphenyl)-1,2,4-oxadiazolidin-3,5-dion-4-ylmethyl] O-(4-butylthiophenyl) S-pentyl dithiolophosphate, S-[2-(3-propoxyphenyl)-1,2,4-oxadiazolidin-3,5-dion-4-ylmethyl] O-(4-hexylthiophenyl) S-hexyl dithiolophosphate, S-[2-(4-butoxyphenyl)-1,2,4-oxadiazolidin-3,5-dion-4-ylmethyl] O-(3-isopropylphenyl) S-propyl dithiolothionophosphate, S-[2-(4-hexyloxyphenyl)-1,2,4-oxadiazolidin-3,5-dion-4-ylmethyl] 4-t-butylphenyl(ethyl)thiolophosphinate, S-[2-(2,6-diethylphenyl)-1,2,4-oxadiazolidin-3,5-dion-4-ylmethyl] diethylthiolothionophosphinate, S-[2-(2,4-dipropylphenyl)-1,2,4-oxadiazolidin-3,5-dion-4-ylmethyl] 4-hexylphenyl(propyl)thiolophosphinate, S-[2-(4-t-butylphenyl)1,2,4-oxadiazolidin-3,5-dion-4-ylmethyl] 4-fluorophenyl(butyl)thiolophosphinate, S-[2-(4-hexylphenyl)-1,2,4-oxadiazolidin-3,5-dion-4-ylmethyl] 4-iodophenyl(hexyl)thiolophosphinate, S-(2-ethyl-1,2,4-oxadiazolidin-3,5-dion-4-ylmethyl) O,O-dihexyloxythiolophosphate, S-(2-propyl-1,2,4-oxadiazolidin-3,5-dion-4-ylmethyl) S,S-dipropyltrithiolophosphate, S-(2-butyl-1,2,4-oxadiazolidin-3,5-dion-4-ylmethyl) N-methyl(ethyl)thiolophosphonamidate, S-(2-pentyl-1,2,4-oxadiazolidin-3,5-dion-4-ylmethyl) N-ethyl(ethyl)thiolophosphonamidate, S-(2-hexyl-1,2,4-oxadiazolidin-3,5-dion-4-ylmethyl) N-isopropyl(ethyl)thiolophosphonamidate, S-(2-phenyl-1,2,4-oxadiazolidin-3,5-dion-4-ylmethyl) O-ethyl N-pentylthiolothionophosphoramidate, S-(2-ethyl-1,2,4-oxadiazolidin-3,5-dion-4-ylmethyl) O-ethyl N,N-diethylthiolothionophosphoramidate, S-(2-propyl-1,2,4-oxadiazolidin-3,5-dion-4-ylmethyl) S-t-butyl N,N-dipropyldithiolothionophosphoramidate, O-(2-methyl-1,2,4-oxadiazolidin-3,5-dithion-4-ylmethyl) O-ethyl phosphoramidate, O-(2-phenyl-1,2,4-oxadiazolidin-3,5-dithion-4-ylmethyl) ethylphosphonamidate and the like.

For practical use as insecticides, the compounds of this invention are generally incorporated into insecticidal compositions which comprise an inert carrier and an insecticidally toxic amount of such a compound. Such insecticidal compositions, which can also be called formulations, enable the active compound to be applied conveniently to the site of the insect infestation in any desired quantity. These compositions can be solids, such as dusts, granules or wettable powders; or they can be liquids such as solutions, aerosols or emulsifiable concentrates.

For example, dusts can be prepared by grinding and blending the active compound with a solid inert carrier such as the talcs, clays, silicas, pyrophyllite and the like. Granular formulations can be prepared by impregnating the compound, usually dissolved in a suitable solvent, onto and into granulated carriers such as the attapulgites or the vermiculites, usually of a particle size range of from about 0.3 to 1.5 mm. Wettable powders, which can be dispersed in water and/or oil to any desired concentration of the active compound, can be prepared by incorporating wetting agents into concentrated dust compositions.

In some cases the active compounds are sufficiently soluble in common organic solvents such as kerosene or xylene so that they can be used directly as solutions in these solvents. Frequently, solutions of insecticides can be dispersed under superatmospheric pressure as aerosols. However, preferred liquid insecticidal compositions are emulsifiable concentrates, which comprise an active compound according to this invention and as the inert carrier, a solvent and an emulsifier. Such emulsifiable concentrates can be extended with water and/or oil to any desired concentration of active compound for application as sprays to the site of the insect infestation. The emulsifiers most commonly used in these concentrates are nonionic or mixtures of nonionic with anionic surface-active agents.

A typical insecticidal composition according to this invention is illustrated by the following example, in which the quantities are in parts by weight.

EXAMPLE 27

Preparation of a Dust

Product of Example 3 : 10
Powdered talc : 90

The above ingredients are mixed in a mechanical grinder-blender and are ground until a homogeneous, free-flowing dust of the desired particle size is obtained. This dust is suitable for direct application to the site of the insect infestation.

The compounds of this invention can be applied as insecticides in any manner recognized by the art. One method for destroying insects comprises applying to the locus of the insect infestation, an insecticidal composition comprising an inert carrier and, as the essential active ingredient, in a quantity which is toxic to said insects, a compound of the present invention. The concentration of the new compounds of this invention in the insecticidal compositions will vary greatly with the type of formulation and the purpose for which it is designed, but generally the insecticidal compositions will comprise from about 0.05 to about 95 percent by weight of the active compounds of this invention. In a preferred embodiment of this invention, the insecticidal compositions will comprise from about 5 to 75 percent by weight of the active compound. The compositions can also comprise such additional substances as other pesticides, stabilizers, spreaders, deactivators, adhesives, stickers, fertilizers, activators, synergists and the like.

The compounds of the present invention are also useful when combined with other insecticides in the insecticidal compositions heretofore described. These other insecticides can comprise from about 5 to about 95 percent of the active ingredients in the insecticidal compositions. Use of the combinations of these other insecticides with the compounds of the present invention provide insecticidal compositions which are more effective in controlling insects and often provide results unattainable with separate compositions of the individual insecticides. The other insecticides with which the compounds of this invention can be used in the insecticidal compositions to control insects, can include halogenated compounds such as DDT, methoxychlor, TDE, lindane, chlordane, isobenzan, aldrin, dieldrin, heptachlor, endrin, mirex, endosulfon, dicofol and the like; organic phosphorus compounds such as TEPP, schradan, ethion, parathion, methyl parathion, EPN, demeton, carbophenothion, phorate, zinophos, diazinon, malathion, mevinphos, dimethoate, DBD, ronnel, oxydemeton-methyl, dicapthon, chlorothion, phosphamidon, naled, fenthion, trichlorofon, DDVP and the like; organic nitrogen compounds such as dinitro-o-cresol, dinitrocyclohexylphenol, DNB, DNP, binapacril, azobenzene and the like; organic carbamate compounds such as carbaryl, ortho 5353 and the like; organic sulfur compounds such as phenothiazine, phenoxathin, lauryl thiocyanate, [bis(2-thiocyanoethyl)ether], isobornyl thiocyanoacetate and the like; as well as such substances usually referred to as fumigants, as hydrogen cyanide, carbon tetrachloride, calcium cyanide, carbon disulfide, ethylene dichloride, propylene dichloride, ethylene dibromide, ethylene oxide, methyl bromide, paradichlorobenzene and the like.

The compounds of the present invention can also be combined with fungicidal and nematocidal chemical compounds to form pesticidal compositions useful for the control of fungi and in some cases soil nematodes as well as insects. Typical examples of such fungicidal chemical compounds are ferbam, nabam, zineb, ziram, thiram, chloranil, dichlone, glyodin, cycloheximide, dinocap, maneb, captan, dodine, PCNB, p-dimethylaminobenzenediazo sodium sulfonate and the like; while examples of nematocidal compounds are chloropicrin, O,O-diethyl O-(2,4-dichlorophenyl) phosphorothioate, tetrachlorothiophene, dazomet, dibromochloropropane and the like.

The new compounds of this invention can be used in many ways for the control of insects. Insecticides which are to be used as stomach poisons or protective materials can be applied to the surface on which the insects feed or travel. Insecticides which are to be used as contact poisons or eradicants can be applied directly to the body of the insect, as a residual treatment to the surface on which the insect may walk or crawl, or as a fumigant treatment of the air which the insect breathes. In some cases, the compounds applied to the soil or plant surfaces are taken up by the plant, and the insects are poisoned systemically.

The above methods of using insecticides are based on the fact that almost all the injury done by insects is a direct or indirect result of their attempts to secure food. Indeed, the large number of destructive insects can be classified broadly on the basis of their feeding habits. Among the insects which can be effectively controlled by the compounds of the present invention are the chewing insects, such as the Mexican bean beetle and the southern armyworm; the piercing-sucking insects, such as the pea aphid, the cereal leaf beetle, the housefly, the grape leafhopper, the chinch bug, the lygus bug, the oyster shell scale, the California red scale, the Florida red scale, the soft scale and mosquitoes; the internal feeders, including borers, such as the European corn borer, the peach twig borer and the corn earworm, worms or weevils, such as the codling moth, the alfalfa weevil, the cotton boll weevil, the pink boll worm, the plum curculio, the red banded leaf roller, the melonworm, the cabbage looper and the apple maggot, leaf miners such as the apple leaf miner, the birch leaf miner and the beet leaf miner, and gall insects such as the wheat joint worm and the grape phylloxera. Insects which attack below the surface of the ground are classified as subterranean insects and include such destructive pests as the wooly apple aphid, the Japanese beetle, the onion maggot and the corn rootworm.

The quantity of active compound of this invention to be used for insect control will depend on a variety of factors, such as the specific insect involved, intensity of the infestation, weather, type of environment, type of formulation and the like. For example, the application of only 1 or 2 ounces of active chemical per acre may be adequate for control of a light infestation of an insect under conditions unfavorable for its feeding, while a pound or more of active compound per acre may be required for the control of a heavy infestation of insects under conditions favorable to their development.

The insecticidal activity of the compounds of the present invention was demonstrated by experiments carried out for the control of a variety of insects.

Southern Armyworm

Foliar portions of potted Dwarf Horticultural bean plants in first true leaf growth stage are sprayed with test solution containing a compound of this invention at the indicated rates, allowed to air dry and removed to holding racks provided with a subterranean water source. Three test plants are used for each test unit. Five third-instar larvae of Southern Armyworm are caged on treated plants for 72 hours. After this time observations are made for insect mortality. The results of this procedure are set forth in Table I.

TABLE I

| Test Compound | Rate (ppm): | Percent Control | | | | |
|---|---|---|---|---|---|---|
| | | 1000 | 512 | 256 | 128 | 64 |
| Product of Ex. 3 | | 7 | — | — | — | — |
| Product of Ex. 4 | | 0 | — | — | — | — |
| Product of Ex. 7 | | 7 | — | — | — | — |
| Product of Ex. 8 | | — | 0 | 10 | 0 | 0 |

Housefly

Approximately 25 to 30 four-day-old Housefly adults are placed in spherical wire mesh cages. The cages are mounted at the center of a rotating turntable so that each cage rotates on its own axis. At least three cages are provided for each test unit. Individual rotating cages are sprayed with respective candidate aerosols at the indicated concentrations. Houseflies are then immediately removed to observation cages, observed for 20- or 60-minute knockdown, supplied with sugar-water food source, transferred to a holding room and observed for mortality 24 hours after treatment. The results of this test are shown in Table II (knockdown:24-hour mortality).

TABLE II

| Test Compound | Rate (ppm): | Percent Control | | | | |
|---|---|---|---|---|---|---|
| | | 1000 | 512 | 256 | 128 | 64 |
| Product of Example 3 | | 5:0 | — | — | — | — |
| Product of Example 4 | | 0:0 | — | — | — | — |
| Product of Example 7 | | 35:21 | — | — | — | — |
| Product of Example 8 | | — | 100:100 | 100:100 | 90:100 | 40:100 |

Mexican Bean Beetle

Foliar portions of potted Dwarf Horticultural bean plants in first true leaf growth stage are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1000 ppm and 50 lbs per acre. Three test plants are used for each test unit. Five third-instar larvae of Mexican Bean Beetle are caged on treated plants for 72 hours. After this time observations are made for insect mortality. The results of these experiments are summarized in Table III.

TABLE III

| Test Compound | Rate ppm : lbs/A: | Percent Control | | | | | | | | |
|---|---|---|---|---|---|---|---|---|---|---|
| | | 1000 50 | 500 — | 256 — | 128 — | 64 — | — 32 | — 16 | — 8 | — 4 |
| Product of Example 3 | | 100 | 100 | 87 | 13 | 0 | 53 | 0 | 0 | 0 |
| Product of Example 4 | | 100 | 100 | 93 | 67 | 47 | 0 | — | — | — |
| Product of Example 7 | | 100 | 100 | 100 | 100 | 33 | 100 | 93 | 67 | 20 |

Green Pea Aphid

Windsor Broad Bean plants grown under greenhouse conditions, in the first true leaf growth stage and in soil of low moisture content are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1000 ppm and 50 lbs/acre. Adult pea aphids are transferred to the foliar portion of the treated plants and held there for a period of 72 hours. After this time insect mortality is determined by observation in comparison to controls. The results of these procedures are shown in Table IV.

TABLE IV

| Test Compound | Rate ppm : lbs/A: | Percent Control | | | | | | | | |
|---|---|---|---|---|---|---|---|---|---|---|
| | | 1000 50 | 500 — | 256 — | 128 — | 64 — | — 32 | — 16 | — 8 | — 4 |
| Product of Example 3 | | 100 | 69 | — | — | — | 77 | 50 | 0 | 0 |
| Product of Example 4 | | 57 | — | — | — | — | — | — | — | — |
| Product of Example 7 | | 99 | 99 | 100 | 97 | 78 | 100 | 99 | 99 | 10 |

Two-Spotted Spider Mite

Potted horticultural beans at growth stage when primary leaves are approximately one inch long are infested with two-spotted spider mites 24 hours prior to treatment, ensuring establishment of adults and egg deposition at time of treatment.

The candidate compound is dissolved in a suitable solvent (acetone, methanol or other) or prepared as a wettable powder and diluted to appropriate concentrations with deionized water containing wetting and/or dispersing agents as appropriate.

Infested host plants, as above, are sprayed with test solution containing a compound of this invention, or the soil of the potted plants is drenched with an aqueous emulsion of the test compound. The pots are then placed in holding racks provided with a subterranean water source. As indicated in the following table, the foliar spray and soil drench are also applied consecutively as one test at 1000 ppm and 50 pounds per acre. Mortality is determined 72 hours after treatment by removing and observing one leaf from each plant. The results of these tests are set forth in Table V.

TABLE V

| Test Compound | Rate ppm: lbs/A: | 1000 50 | 500 — | 256 — | 128 — | 64 — | — 32 | — 16 | — 8 | — 4 |
|---|---|---|---|---|---|---|---|---|---|---|
| Product of Example 3 | | 100 | 100 | 100 | 69 | 28 | 100 | — | — | — |
| Product of Example 4 | | 100 | 100 | 100 | 100 | 46 | 0 | — | — | — |
| Product of Example 7 | | 100 | 100 | 100 | 100 | 98 | 100 | 100 | 93 | 53 |

Southern Corn Rootworm

Two germinating corn seeds and two ml of test compound formulated at the indicated concentrations are placed in plastic cups equipped with perforated cardboard covers. After 30 minutes 5 grams of soil mix (loam:sand, 2:1) are added to the cup and the contents are mixed. Five Southern Corn Rootworm larvae are then placed on the surface of the soil. The cups are then covered and held for four-day mortality observations. The results of this procedure can be seen in Table VI.

TABLE VI

| Test Compound | Rate (lbs/acre): | 64 | 32 | 16 | 4 |
|---|---|---|---|---|---|
| Product of Example 3 | | 73 | — | — | — |
| Product of Example 4 | | 100 | 100 | 100 | 13 |
| Product of Example 7 | | 93 | 80 | 7 | 0 |

Boll Weevil

Two leaves of a cotton plant are sprayed with test solution containing a compound of this invention at the indicated rate and are allowed to air dry. Boll weevils are then placed on the surface of the leaves and the infested leaves are kept in a petri dish and are held for a period of 48 hours. After this time mortality is observed and compared to untreated controls.

In the soil drench application 14-day-old cotton plants are watered with 30 ml of the product of Example 4 at 32 lbs/acre. After 48 hours the primary leaves are removed and each is placed in a container with 10 adult cotton Boll Weevils. Forty-eight hours after infestation mortality is observed and compared to untreated controls.

The results of these tests are shown in Table VII.

TABLE VII

| Test Compound | Rate ppm: lbs/A: | 512 — | 500 — | 256 — | 128 — | 64 — | — 32 |
|---|---|---|---|---|---|---|---|
| Product of Example 4 | | — | 63 | — | — | — | 0 |
| Product of Example 8 | | 50 | — | 30 | 20 | 0 | — |

Cabbage Looper

Ten- to fourteen-day-old Henderson bush lima bean plants are planted in 3½ inch plastic pots using potting soil capped with ¼ inch of sand. The bean plants are then placed on a turntable and are sprayed with 100 ml of an aqueous solution or dispersion of the product of Example 8 at the indicated concentrations. The plants are then allowed to dry. A leaf is removed from the bean plant and is placed in a petri dish on top of a piece of wetted filter paper. Ten third-instar larvae of the Cabbage Looper are then placed on the leaf, and the petri dish is covered. Observations of mortality are made after 48 hours and are compared to untreated controls. Results of this test are shown in Table VIII.

TABLE VIII

| Test Compound | Rate (ppm): | 512 | 256 | 128 | 64 |
|---|---|---|---|---|---|
| Product of Example 8 | | 30 | 0 | 0 | 0 |

Yellow Fever Mosquito Larvae

Aliquots of 100 ml of tap water containing various concentrations of the product of Example 8 are each supplied with 20 1-day-old Yellow Fever Mosquito larvae (aedes aegypti L.). The larvae are maintained at 25° C and are fed with malt yeast powder. After 13 days, when the pupae of untreated insects have hatched, the mortality percentages are calculated in comparison with the untreated controls. The results are indicated in Table IX.

TABLE IX

| Test Compound | Rate (ppm): | 10 | 1 | 0.1 | 0.01 |
|---|---|---|---|---|---|
| Product of Example 8 | | 100 | 100 | 90 | 70 |

We claim:
1. A new compound of the formula

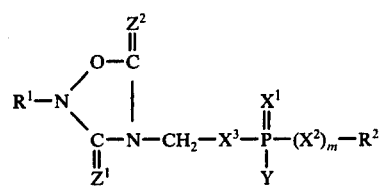

wherein $R^1$ and $R^2$ are independently selected from the group consisting of lower alkyl and

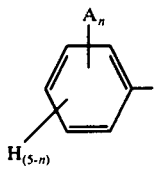

wherein A is selected from the group consisting of lower alkyl, lower alkoxy, lower alkylthio and halogen and $n$ is an integer from 0 to 2; $X^1$, $X^2$, $X^3$, $Z^1$ and $Z^2$ are independently selected from the group consisting of oxygen and sulfur; $m$ is the integer 0 or 1; and Y is selected from the group consisting of lower alkyl, lower alkoxy, lower alkylthio, amino, lower alkylamino and di (lower) alkylamino.

2. The compound of claim 1, S-(2-phenyl-1,2,4-oxadiazolidin-3,5-dion-4-ylmethyl) O-methyl N-isopropylthiolophosphoramidate.

3. The compound of claim 1, S-(2-phenyl-1,2,4-oxadiazolidin-3,5-dion-4-ylmethyl) O,O-diethylthiolothionophosphate.

4. The compound of claim 1, S-(2-methyl-1,2,4-oxadiazolidin-3,5-dion-4-ylmethyl) O-methyl N-isopropylthiolophosphoramidate.

5. The compound of claim 1, S-(2-methyl-1,2,4-oxadiazolidin-3,5-dion-4-ylmethyl) O,O-diethylthiolothionophosphate.

6. The compound of claim 1, S-[2-(4-methylphenyl)-1,2,4-oxadiazolidin-3,5-dion-4-ylmethyl] O-(3,4-dichlorophenyl) N,N-dimethylthiolophosphoramidate.

7. The compound of claim 1, S-[2-(4-methoxyphenyl)-1,2,4-oxadiazolidin-3,5-dion-4-ylmethyl] S-(4-methylphenyl) O-methyl dithiolophosphate.

8. The compound of claim 1, S-[2-(3-methylthiophenyl)-1,2,4-oxadiazolidin-3,5-dion-4-ylmethyl] S-ethyl O-(4-methoxyphenyl) dithiolophosphate.

9. An insecticidal composition comprising an inert carrier and, as an essential active ingredient, in a quantity toxic to insects, a compound of claim 1.

10. A method of controlling insects which comprises contacting said insects with an insecticidal composition comprising an inert carrier and, as an essential active ingredient, in a quantity toxic to insects, a compound of claim 1.

* * * * *